Figure 1:
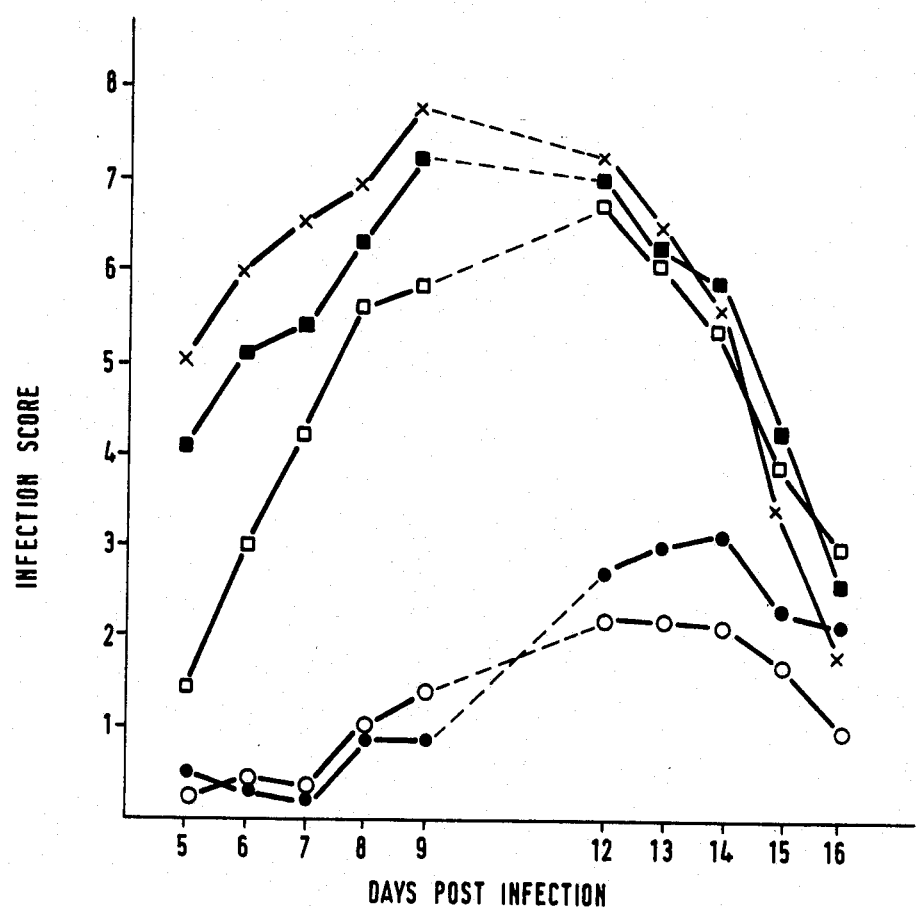

United States Patent [19]

Hunter et al.

[11] Patent Number: 4,790,989

[45] Date of Patent: Dec. 13, 1988

[54] TREATMENT OF FUNGAL INFECTIONS

[75] Inventors: Pamela A. Hunter; Valerie Berry, both of Betchworth; Joshua Oduro-Yeboah; Norman A. Orr, both of Worthing, all of England

[73] Assignee: Beecham Group p.l.c., England

[21] Appl. No.: 36,929

[22] Filed: Apr. 10, 1987

[30] Foreign Application Priority Data

Jun. 26, 1986 [GB] United Kingdom ............... 8615669
Dec. 11, 1986 [GB] United Kingdom ............... 8629641

[51] Int. Cl.$^4$ ................... C07D 309/10; A01H 25/34
[52] U.S. Cl. ................... 424/404; 514/404; 514/451; 514/723; 514/969
[58] Field of Search ............... 514/404, 451, 723; 424/404

[56] References Cited

U.S. PATENT DOCUMENTS 4,524,075 6/1985 Oduro-Yeboah .................. 514/723

FOREIGN PATENT DOCUMENTS 540123 6/1977 Japan.

OTHER PUBLICATIONS

G. Mellows, Bactroban (mupirocin): Proceedings of an International Symposium, Excerpta Medica (1985), pp. 3–10.
R. Aly, Ibid, pp. 72–77.

Primary Examiner—Thurman K. Page
Assistant Examiner—P. J. Ryan
Attorney, Agent, or Firm—Jacobs & Jacobs

[57] ABSTRACT

Certain formulations of pseudomonic acids and their salts have good antifungal activity.

10 Claims, 2 Drawing Sheets

TREATMENT OF FUNGAL INFECTIONS

The present invention relates to the treatment of fungal infections.

Mupirocin formerly known as pseudomonic acid or pseudomonic acid A, is a compound of the formula I:

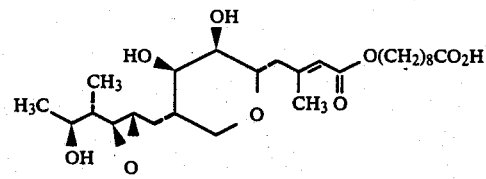

obtained, interalia, by aerobically culturing *Pseudomonas fluorescens*. Mupirocin, its salts and esters, and its antibiotic acitivity are described in U.S. Pat. No. 4,071,536 and GB No. 1 395 907.

Pseudomonic acid B (formerly known as pseudomonic acid I), pseudomonic acid C and pseudomonic acid D may also be obtained by culturing *Pseudomonas fluorescens* and are of formulae II, III and IV, respectively:

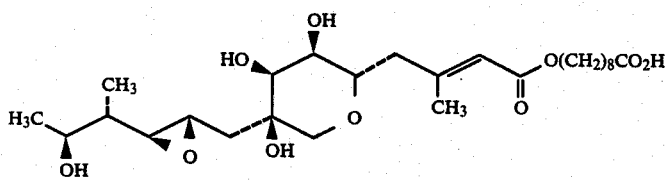

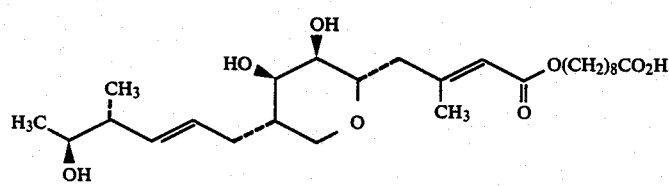

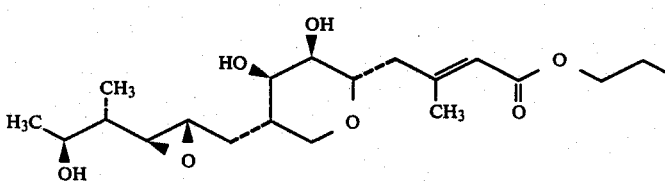

These compounds and their antibacterial activity are described in GB No. 1 395 907, EP Nos. 0 003 069, and 0 068 680, respectively. See also U.S. Pat. Nos. 4,071,536, 4,205,002 and 4,226,880.

Lithium pseudomonate, i.e. the lithium salt of mupirocin, is described in U.S. Pat. No. 4,639,534 and EP No. 0 005 614 as an intermediate in the purification of mupirocin. Silver pseudomonate, and crystalline calcium pseudomonate and hydrates thereof, are described in EP Nos. 0 128 338 and 0 167 856, respectively.

The use of mupirocin and its salts and esters in treating respiratory, venereal and mycoplasma-induced diseases in mammals is described in U.S. Pats. Nos. 4,196,214 and 4,206,224 and GB 1 577 730, and their use in treating swine-dysentery is described in U.S. Pat. No. 4,186,206 and GB 1 577 545.

Topical formulations comprising mupirocin or a salt or ester thereof, and at least 1% by weight of a poly(-substituted or unsubstituted alkylene)glycol, for example a polyethylene glycol, or a derivative thereof, are described in U.S. Pat. No. 4,524,075 and EP No. 0 095 897.

One such topical formulation, that is to say, a formulation of mupirocin free acid (2%) in a polyethylene glycol base, known as 'Bactroban' (Trade Mark - Beecham Group p.l.c.), has been reported as showing some activity against certain fungal infections ('Bactroban (mupirocin)': Proceedings of an International Symposium, Nassau, May 21-22, 1984; Editors: R. L. Dobson et al, Excerpta Medica, Current Clinical Practice Series 16, 1985—R. Aly, p. 72; J. H. Levenstein et al, p.141; J. Hewitt et al, p. 190; D. C. DeBoer, p. 224; and E. W. Rosenberg, p. 257). It is not possible from those reports, however, to ascertain whether the disappearance of the fungal infection is attributable to the mupirocin, the polyethylene glycol base, or the natural defences of the body.

It has also previously been reported that a substance produced by *Pseudomonas fluorescens* inhibits the growth of certain bacteria and fungi, although fungi are more resistant to the inhibitory substance than bacteria ('Bactroban (mupirocin)' op. cit., G. Mellows, p.3, and references cited therein).

A formulation of mupirocin in "an ointment base of white soft paraffin lanolin and wool fat" (sic) has been described for the treatment of nasal bacterial infections ('Mupirocin, a novel topical antibiotic: Proceedings of a Symposium, Jersey, April 1984; Editors: D. S. Wilkinson et al, Royal Society of Medicine, International Congress and Symposium Series, No. 80, 1984, London—M. W. Casewell et al, p.149).

It has now been found that certain formulations of, pseudomonic acids and their salts have improved antifungal activity and are therefore of value in the treatment of fungal infections in animals, including numans.

Accordingly, the present invention provides a method for the treatment of a fungal infection, which comprises applying topically to a patient an antifungally effective amount of a topical pharmaceutical or veterinary composition comprising a pseudomonic acid or a non-toxic salt thereof, and a pharmaceutically or veterinarily acceptable carrier, the pseudomonic acid or salt thereof being present in an amount that, in use, corresponds to at least the saturation solubility of the pseudomonic acid or salt in the carrier at ambient temperature.

The present invention also provides the use of a pseudomonic acid or a non-toxic salt thereof for the preparation of a pharmaceutical or veterinary medicament comprising a pseudomonic acid or a non-toxic salt thereof, and a pharmaceutically acceptable carrier, for the treatment of fungal infections, the pseudomonic acid or salt thereof being present in an amount that, in use, corresponds to at least the saturation solubility of the pseudomonic acid or salt in the carrier at ambient temperature.

The expressions 'a pseudomonic acid' and 'pseudomonic acids' as used herein include mupirocin (pseudomonic acid A) and also pseudomonic acids B, C and D. Suitably, the pseudomonic acid used according to the present invention is mupirocin.

A non-toxic salt of a pseudomonic acid used according to the invention is, in particular, a pharmaceutically acceptable or veterinarily acceptable salt.

Examples of suitable non-toxic, pharmaceutically or veterinarily acceptable salts of the pseudomonic acids for use according to the present invention include metal salts, e.g. aluminium salts, silver salts, alkali metal salts (e.g. sodium or potassium salts), alkaline earth metal salts (e.g. calcium or magnesium salts), and ammonium salts, and substituted ammonium salts, for example those with lower alkylamines (e.g. triethylamine), hydroxy-lower alkylamines (e.g. 2-hydroxyethylamine), di(2-hydroxyethyl)amine or tri(2-hydroxyethyl)amine), cycloalkylamines (e.g. dicyclohexylamine), or with procaine, and also dibenxylamine, N,N-dibenxylenthylenediamine, 1-ephenamine, N-ethylpiperidine, N-benzyl-$\beta$-phenethylamine, dehydroabietylamine, N,N'-bisdehydroabietylethylene-diamine, and bases of the pyridine type (e.g. pyridine, collidine and quinoline). The lithium salt is also suitable for certain purposes, including certain pharmaceutical and veterinary purposes.

In general, the salts may be anhydrous or may be in the form of pharmaceutically or veterinarily acceptable solvates, such as alcoholates, and, especially, hydrates.

Preferred salts include the silver, calcium and lithium salts. In the case of the calcium salt of mupirocin, advantageously the crystalline calcium salt, preferably the crystalline hydrated calicum salt, and especially the crystalline calicum salt dihydrate, is used. The crystalline calcium salt dihydrate may contain from 1.8 to 2.2 moles, normally from 1.9 to 2.1 moles, of water per mole.

The pseudomonic acids may also suitably be used in free acid form according to the present invention.

Preferably, the composition or medicament used according to the invention comprises mupirocin, the calcium salt thereof, or the silver salt thereof.

The composition or medicament used according to the invention comprises the pseudomonic acid or non-toxic salt thereof in an amount that, in use, corresponds at least to (that is, it equals or exceeds) its saturation solubility (at ambient temperature; say, at 20° C.) in the particular carrier used as the vehicle base for the particular composition or medicament. Preferably, the said amount exceeds the said saturation solubility, in which case the amount of excess pseudomonic acid or salt present in the composition or medicament above the saturation solubility may, in use, be present in undissolved form or may be present in dissolved form to give a super-saturated solution.

In the former case, where the composition in use contains undissolved pseudomonic acid or salt, the composition as manufactured and sold will generally also contain such undissolved material. Compositions containing excess undissolved pseudomonic acid or salt for use according to the present invention include not only, for example, creams, lotions and ointments containing undissolved material in suspension, but also, for example, powder formulations (including dusting powders and spray powders) in which pulverulent active material is admixed with a pulverulent carrier (for example, talc). It will be appreciated that since the pseudomonic acid or salt has zero or negligible solubility in, say, talc, it will necessarily be present in an excess amount exceeding such solubility.

In the case where the composition in use contains the excess pseudomonic acid or salt in dissolved form as a super-saturated solution, such super-saturation will generally occur in situ and the composition as manufactured and sold will be in a form differing from that or the composition in use.

Compositions designed to produce super-saturated solutions of a drug in situ are known and the use of such compositions is within the scope of the present invention. Such compositions may initially contain a sub-saturated or saturated drug solution, which produces a super-saturated solution either on, or immediately prior to, application to the body. One such composition comprises a sub-saturated solution of the drug in a mixture of volatile and non-volatile solvents; on topical application the volatile solvent evaporates thus increasing the concentration to a super-saturated level (*J. Pharm. Sci.*, 58 9 (1969), 1098–1102). Another such composition comprises two phases, which are mixed to form a super-saturated solution immediately prior to application as described in EP No. 0 151 953 (Beecham).

It has been found that the presence of such excess, undissolved or super-saturated, pseudomonic acid or salt gives substantially improved antifungal efficacy, as compared with compositions or medicaments in which the pseudomonic acid or salt is present in a sub-saturated amount at the same concentration.

The composition or medicament should contain the pseudomonic acid or salt in an amount of at least 100% by weight, advantageously at least 101% by weight, preferably at least 110% by weight, especially at least 125% by weight, and more especially at least 150% by weight, of its saturation solubility in the carrier at ambient temperature.

Subject to the saturation requirement discussed above, the composition or medicament used according to the invention may comprise from 0.01 to 99% of pseudomonic acid or a non-toxic salt thereof, suitably from 0.01 to 50%, preferably from 0.1 to 25%, more preferably from 0.5 to 10%, and especially from 1 to 3%.

(All percentages mentioned herein are by weight and based on the total weight of the composition or medicament. Percentages of the pseudomonic acid salts given herein are calculated as the free acid.)

In a preferred aspect of the invention, the composition or medicament comprises from 1 to 3% of mupirocin as the hydrated crystalline calcium salt.

Preferably the pseudomonic acid or salt thereof is incorporated in the composition or medicament in the form of fine particles having an average size (diameter) of less than 50 μm.

The composition or medicament for use according to the present invention may, for example, be presented in the form of a cream, a lotion, an ointment, a dusting powder, or a spray (for example an aerosol spray emitting a powder or foam), as well as other conventional topcial application formulations.

One suitable composition or medicament for use according to the present invention cmprises the pseudomonic acid or salt thereof in conjunction with soft paraffin and lanolin or derivative or synthetic equivalent thereof.

The term 'soft paraffin' as used herein includes the cream or ointment bases white soft paraffin and yellow soft paraffin.

The term 'lanolin' as used herein includes native wool fat and purified wool fat. Derivatives of lanolin include, in particular, lanolins which have been chemically modified in order to alter their physical or chemical properties. Synthethic equivalents of lanolin include, in particular, synthetic or semisynthetic compounds and mixtures which are known and used in the pharmaceutical and cosmetic arts as alternatives to lanolin and may, for example, be referred to as 'lanolin substitutes'.

One suitable synthetic equivalent of lanolin is the material available under the Trade Mark 'Softisan' known as 'Softisan 649'. Softison 649, available from Dynamit Nobel Aktiengesellschaft, is a glycerin ester of natural vegetable fatty acids, of isostearic acid and of adipic acid; its properties are discussed by H. Hermsdorf in *Fette, Seifen, Anstrichmittel*, Issue No. 84, No. 3 (1982), p.p. 3–6.

Suitably such a composition or medicament comprises from 25 to 99% of the soft paraffin, preferably from 50 to 98%, more preferably from 75 to 95%. Suitably the composition or medicament comprises the lanolin or derivative or synthetic equivalent thereof in an amount of from 1 to 25%, preferably from 1 to 15%, more preferably from 3 to 7%. In addition, such a composition or medicament may contain liquid paraffin in an amount of from 0 to 20%.

The term 'liquid paraffin' as used herein includes any form of liquid paraffin suitable for pharmaceutical or veterinary topical use.

One particularly suitable such composition or medicament for use according to the present invention comprises from 1 to 3% of mupirocin or a salt thereof, from 65 to 96% (preferably from 75 to 96%) of white soft paraffin, from 0 to 15% of liquid paraffin, and from 3 to 7% of lanolin or a derivative or synthetic equivalent thereof. Such a composition may suitably be presented as a cream or ointment for application to the skin.

A second particularly suitable composition or medicament for use according to the present invention comprises from 1 to 3% of mupirocin or a salt thereof, from 25 to 60% of liquid paraffin, from 20 to 50% of water, from 3 to 30% (preferably from 10 to 30%) of emulsifier, and, optionally, one or more conventional auxiliaries, such as a preservative. Such a composition may suitably be presented as a cream or lotion for application to the skin.

Suitable emulsifiers for use in such a composition or medicament include, for example, stearyl alcohol, cetyl alcohol, polyoxyethylene alcohols having surfactant properties (for example, Cetomacrogol 1000), and other surfactants conventionally used as emulsifiers in pharmaceutical preparations, especially in creams.

Suitable preservatives for use in such a composition or medicament include, for example, phenoxyethanol, and other preservatives conventionally used in pharmaceutical preparations, especially in creams.

The composition or medicament used according to the present invention may comprise additional therapeutic agents such as antimicrobial, antibiotic, antibacterial, antifungal, antiviral, and antiinflammatory agents, for example from 1 to 3% of chlortetratcycline, idoxuridine, or phenazone, provided that such additional components are compatible with the pseudomonic acid or salt thereof and the other components. Pseudomonic acids and salts thereof show a tendency to undergo rearrangement reactions in the presence of acids and accordingly acidic agents are unlikely to be compatible with pseudomonic acids and salts therof.

The compositions or medicaments may also comprise appropriate conventional additives, for example preservatives, emulsifiers, solvents to assist drug penetration, and emollients.

The compositions and medicaments used according to the invention may be produced by conventional pharmaceutical or veterinary techniques. Thus, for example, ointments and creams may conveniently be prepared by mixing together at an elevated temperature, preferably 60°–70° C., the components constituting the vehicle. The mixture may then be cooled to room temperature, and, after addition of any further ingredients, stirred to ensure adequate dispersion. The pseudomic acid or salt thereof may be added during the hot preparation of the base, or may be added together with the additional ingredients after cooling of the base.

A suitable sterilisation precedure may be included in the above procedure if necessary. Alternatively raw materials may be obtained in sterile condition and the formulation or medicament may be produced aseptically.

If necessary the composition or medicament may be milled at any suitable stage of the process.

The compositions and medicaments comprising pseudomonic acids and their salts used according to the invention are antifungally active, in particular against filamentous fungi. They are useful in combating fungal infections in animals, including humans. They may, for example, be used in treating topical fungal infections in man caused by, anong other organisms, species of Trichophyton, Trichosporon, Hendersonula, Microsporum, Epidermophyton, and Pityrosporum. They may also be used in the treatment of a variety of other fungal infections caused by, for example Aspergillus, Coccidioides, Paracoccidioides, Histoplasma and Blastomyces species.

The following examples illustrate the present invention. Examples 1 and 2 illustrate the range of antifungal activity of mupirocin and its salts in vitro. Examples 3 to 9 illustrate various compositions or medicaments suitable for use according to the present invention. Examples 10 and 11 illustrate the activity of compositions or medicaments according to the present invention in vivo.

Throughout the examples, the amounts of mupirocin specified are calculated as the free acid (f.a.), irrespective of whether used in the form of the free acid or a salt.

The following trade names are used in the examples:

'Softisan 649'—a glycerin ester of natural vegetable fatty acids, of isostearic acid and of adipic acid (Dynamit Nobel AG).

'Softisan 378'—triglyceride mixture derived form selected saturated $C_8$–$C_{10}$ coconut oil fatty acids (Dynamit Nobel AG).

'Softisan 601'—mixture of triglycerides and partial glycerides of natural vegetable fatty acids (Dynamit Nobel AG).

'Promulgen G'—stearyl alcohol and ethoxylated cetostearyl alcohol.

'Oleth 10'—10 mole ethoxylate of oleyl alcohol.

'Imwitor 960 K'—self-emulsifying mixture of partial glycerides of natural palmitic and stearic acids with an anionically active emulsifier.

EXAMPLE 1

Antifungal activity of mupirocin salts in vitro

The sodium, lithium and calcium salts of mupirocin (pseudomonic acid A) were tested against several organisms at 500 μg/ml using a zone diffusion assay with wells cut in seeded agar. Zones of inhibition thus obtained were measured after incubation for 1–3 days at 30°–37° C., and the results are summarised in Table 1 below.

TABLE 1

| Organism | Zone diameter (mm) | | |
|---|---|---|---|
| | Sodium salt | Lithium salt | Calcium salt |
| Aspergillus niger | 37 | 37 | 37 |
| Hendersonula toruloidea TH65 | 33 | 34 | 33 |
| Trichophyton mentagrophytes 569A | 21 | 21 | 21 |

EXAMPLE 2

Antifungal activity of mupirocin and calcium salt in vitro

The calcium salt and free acid forms of mupirocin were tested against several organisms as described in Example 1. The results are summarised in Table 2 below.

TABLE 2

| Organism | Zone diameter (mm) | |
|---|---|---|
| | Calcium salt | Free acid |
| Aspergillus niger | 40 | 40 |
| Epidermophyton floccosum | 30 | 29 |
| Hendersonula toruloidea TH65 | 35 | 35 |
| Microsporum persicolor TH53 | 20 | 20 |
| Paecilomyces varioti | 42 | 42 |
| Trichophyton interdigitale TH3 | 21 | 21 |
| Trichopyton mentagrophytes 569A | 28 | 28 |
| Trichosporon cutaneum MR1 | 38 | 38 |

EXAMPLE 3

Ointment Formulation

| | % w/w |
|---|---|
| mupirocin | 2.0 |
| white soft paraffin | 82.76 |
| wool fat | 4.9 |
| liquid paraffin | 10.34 |

An ointment formulation was prepared from the above ingredients by the following method:

Appropriate proportions of white soft paraffin, liquid paraffin and wool fat were heated together until molten (60°–70° C.) and mixed thoroughly. The mixture was allowed to cool down, with stirring, to room temperature and micronised mupirocin was incorporated using a suitable mixer. The ointment was finally triple-roller-milled to disperse the mupirocin.

Less than 1% of the mupirocin present in the ointment was dissolved in the base, the remainder being present as undissolved excess (as measured at 20° C.).

EXAMPLE 4

Ointment Formulation

| | % w/w |
|---|---|
| mupirocin | 2.0 |
| white soft paraffin | 93.1 |
| 'Softisan 649' | 4.9 |

An ointment formulation was prepared from the above ingredients by the following method:

Appropriate proportions of white soft paraffin and 'Softisan 649' were heated together until molten (60°–70° C.) and mixed thoroughly. The mixture was allowed to cool down, with stirring, to room temperature and micronised mupirocin was incorporated using a suitable mixer. The ointment was finally triple-roller-milled to disperse the mupirocin.

Less than 1% of the mupirocin present in the ointment was dissolved in the base, the remainder being present as undissolved excess (as measured at 20° C.).

EXAMPLE 5

Ointment Formulation

| | % w/w |
|---|---|
| mupirocin, crystalline calcium salt, dihydrate | 2.0 (f.a.) |
| white soft paraffin | 93.1 |
| 'Softisan 649' | 4.9 |

An ointment formulation was prepared from the above ingredients by the following method:

Appropriate proportions of white soft paraffin and 'Softisan 649' were heated together until molten (60°–70° C.) and mixed thoroughly. Micronised calcium mupirocin was incorporated using a suitable mixer and then the mixture was allowed to cool down, with sitrring, to room temperature. The ointment was finally triple-roller-milled to disperse the calcium mupirocin.

Less than 1% of the calcium mupirocin present in the ointment was dissolved in the base, the remainder being present as undissolved excess (as measured at 20° C.).

EXAMPLE 6

Cream formulation

| | % w/w |
|---|---|
| mupirocin, crystalline calcium salt, dihydrate | 2.0 (f.a.) |
| cetomacrogol 1000 | 3.6 |
| stearyl alcohol | 16.4 |
| phenoxyethanol | 1.0 |
| water | 35.0 |
| liquid paraffin | to 100.0 |

A cream formulation was prepared from the above ingredients by the following method:

Appropriate proportions of cetomacrogol, stearyl alcohol and liquid paraffin were heated until molten (60°–70° C.). Calcium mupirocin and phenoxyethanol were added and dispersed. An appropriate quantity of water was then mixed with the oil phase, after being heated to a similar temperature. The mixture was homogenised and then cooled to about 40° C., while being stirred. A vacuum was then applied and stirring was continued until the cream reached room temperature.

Less than 30% of the calcium mupirocin present in the cream was dissolved in the base, the remainder being present as undissolved excess (as measured at 20° C.).

EXAMPLE 7

Cream formulation

| | % w/w |
|---|---|
| mupirocin, crystalline calcium salt, dihydrate. | 4.0 (f.a) |
| methyl glucose dioleate | 1.0 |
| 'Promulgen G' | 6.0 |
| 'Oleth - 10' | 3.5 |
| liquid paraffin | 48.9 |
| 'Softisan 649' | 10.0 |
| Imidurea USNF | 0.3 |
| methyl p-hydroxybenzoate | 0.2 |
| propyl p-hydroxybenzoate | 0.1 |
| water | to 100.0 |

A cream formulation is prepared from the above ingredients by the following method:

Appropriate quantities of methyl glucose dioleate, Promulgen G, Oleth-10, liquid paraffin and Softisan 649 were heated until molten (60°–65° C.). Methyl p-hydroxy benzoate and propyl p-hydroxybenzoate were then dispersed and the major portion of the required quantity of water was mixed with the oil phase, after being heated to a similar temperature. The mixture was homogenised and cooled to about 40° C. The Imidurea was then added, dissolved in the remainder of the aqueous phase. A vacuum was applied and stirring was continued until the cream reached room temperature.

Part of the calcium mupirocin was present as undissolved material in excess of its saturation solubility in the base.

EXAMPLE 8

Cream formulation

| | % w/w |
|---|---|
| mupirocin, crystalline calcium salt, dihydrate | 2.0 (f.a) |
| 'Softisan 378' | 25.0 |
| 'Softisan 601' | 20.0 |
| 'Imwitor 960 K' | 5.0 |
| 4-chloro-m-cresol | 0.2 |
| water | to 100.0 |

A cream formulation is prepared from the above ingredients by the following method:

Appropriate quantities of Softisan 378, Softisan 601 and Imwitor 960K were heated until molten (65°–70° C.). The 4-chloro-m-cresol was dissolved in the required quantity of water and mixed with the oil phase, after being heated to a similar temperature. The mixture was homogenised and then cooled to about 40° C. while being stirred. A vacuum was applied and stirring was continued until the cream reached room temperature.

Part of the calcium mupirocin was present as undissolved material in excess of its saturation solubility in the base.

EXAMPLE 9

Cream formulation

| | % w/w |
|---|---|
| mupirocin, crystalline calcium salt, dihydrate | 5.0 (f.a) |
| cetomacrogol 1000 | 1.8 |
| cetostearyl alcohol | 7.2 |
| liquid paraffin | 6.0 |
| white soft paraffin | 15.0 |
| 4-chloro-m-cresol | 0.1 |
| water | to 100.0 |

This cream formulation corresponds to Cetomacrogol Cream BP - Formula A. The cream base is prepared by the standard British Pharmacopoeia 1980 method. Micronised calcium mupirocin is then added to the cream and incorporated using a suitable mixer.

Part of the calcium mupirocin was present as undissolved material in excess of its saturation solubility in the base.

EXAMPLE 10

Antifungal activity of mupirocin formulations in vivo

Formulations of mupirocin free acid and mupirocin calcium salt in an ointment base used according to the invention have been tested for their effect on ringworm in guinea pigs, and have been cmpared with a formulation of mupirocin free acid in a polyethylene glycol base.

An area of each flank of each guinea pig was shaved and depilated. 24 hours later, each flank was lightly scarified with a blunted scapel blade and a freshly prepared suspension of Trichophyton mentagrophytes (mycelium and spores) was spread onto the scarified area (Day 0). The guinea pigs were divided into six groups of six pigs each of differing treatments. Topical therapy was commenced 24 hours after infection by application of the following formulations to the infected area, and was continued once daily for seven days (Days 1 to 7).

In each case only one flank of the guinea pig was treated, the second flank being left untreated for comparison.

Group 1: No treatment—control.
Group 2: Mupirocin free acid (2%) in a polyethylene glycol (PEG) base—comparison (all mupirocin present was dissolved in the base: the mupirocin content amounted to about 15% of the saturation solubility).
Group 3: Polyethylene glycol base alone (placebo PEG)—comparison.
Group 4: Mupirocin free acid (2%) in ointment base (OB) according to the invention (cf. Example 4).
Group 5: Mupirocin calcium salt (2%, f.a.) in ointment base (OB) according to the invention (cf. Example 5).
Group 6: Ointment base (OB) alone (placebo OB) (prepared according to Example 4 with omission of mupirocin)—comparison.

Clinical evaluation was commenced on Day 5 and continued at intervals. A score (on a scale of 0-8) was assigned to each infected area based on erythema, alopecia, scaling and scabbing, taking into account both the size of the infected area and the severity of the symptoms. The mean score was determined for each group of guinea pigs and is shown in the accompanying FIG. 1, which is a graph showing the mean infection score against time for each of the groups of guinea pigs. (The performance of the two placebos PEG and OB was so similar that they have been plotted together).

It can be seen from FIG. 1 that the two groups of guinea pigs treated according to the present invention (Groups 4 and 5) showed markedly less infection than not only the untreated control group and the two placebo-treated groups, but also the group treated with the mupirocin/polyethylene glycol formulation. In fact, the overall effect achieved by the mupirocin/polyethylene glycol formulation was not better than that achieved by the placebos or in the untreated control group: although there was an initital slight suppression of infection, the response was transient and the infection flared up when treatment was terminated. In contrast thereto, treatment according to the present invention showed good suppression of the infection.

Additionally, on Days 7 and 9, skin and hair samples were taken from all animals and inspected microscopically for the presence of *Trichophyton mentagrophytes*. Table 3 below indicates the number of animals (out of 6 in each group) where the organism wash detected.

TABLE 3

| Group | Number of infected animals | |
|---|---|---|
| | Day 7 | Day 9 |
| 1. Untreated control | 6 | 6 |
| 2. Mupirocin free acid/PEG | 3 | 3 |
| 3. Placebo PEG | 6 | 6 |
| 4. Mupirocin free acid/OB | 1 | 2 |
| 5. Mupirocin Ca salt/OB | 0 | 1 |
| 6. Placebo OB | 6 | 6 |

These results again demonstrate the effective control of the infection by the treatment according to the present invention.

EXAMPLE 11

Antifungal activity of mupirocin formulation in vivo

The procedure of Example 10 was repeated using three groups of six guinea pigs each, treated as follows:
Group 1: No treatment—control.
Group 2: Mupirocin calcium salt (2%, f.a) in cream base (CB) according to the invention (cf. Example 3).
Group 3: Cream base (CB) alone (placebo CB) (prepared according to Example 3 with omission of mupirocin)—comparison.

Figure 2:
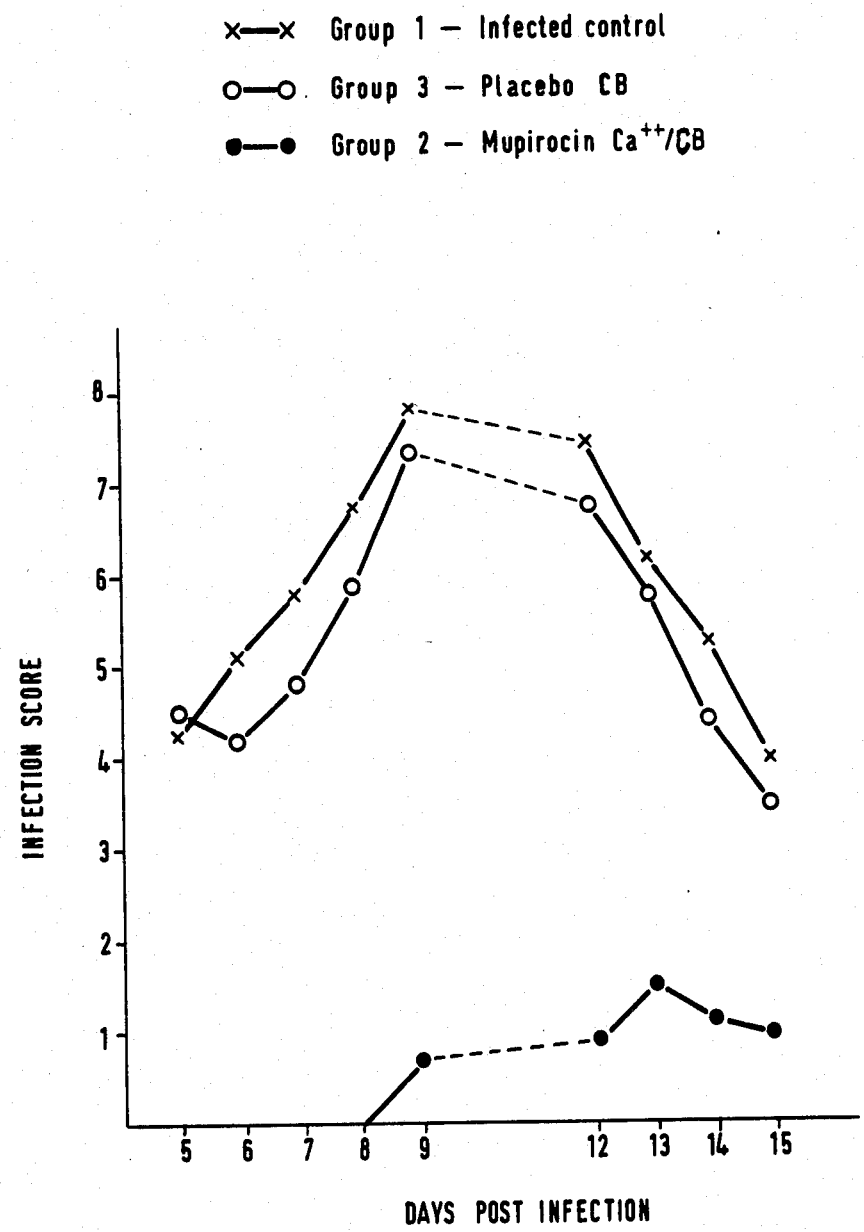

The mean infection scores are shown in FIG. 2, from which it can again be seen that the group treated according to the present invention (Group 2) showed good suppression of infecton compared with both the untreated control group and the placebo-treated group, and also compared with the group treated with the mupirocin/polyethylene glycol formulation (Group 3 of Example 7).

In this example, skin and hair samples were taken on Days 5, 7 and 9, from both the untreated (left - L) flank and the treated (right - R) flank of all animals, and examined as in Example 7. The results are summarised in Table 4.

TABLE 4

| Group | Flank | Number of infected animals | | |
|---|---|---|---|---|
| | | Day 5 | Day 7 | Day 9 |
| 1. Untreated Control | L | 6 | 6 | 6 |
| | R | 6 | 6 | 6 |
| 2. Mupirocin Ca Salt/CB | L | 6 | 6 | 6 |
| | R | 0 | 0 | 1 |
| 3. Placebo CB | L | 6 | 6 | 6 |
| | R | 5 | 6 | 6 |

These results again demonstrate the effective control of the infecton by the treatment according to the present invention.

We claim;

1. A method for the treatment of a fungal infection, which comprises applying topically to a patient an antifungally effective amount of a topical pharmaceutical or veterinary composition comprising a pseudomonic acid or a non-toxic pharmaceutically or veterinary acceptable salt thereof, and a pharmaceutically or veterinary acceptable carrier, the pseudomonic acid or salt thereof being present in an amount that, in use, corresponds to at least the saturation solubility of the pseudomonic acid or salt in the carrier at ambient temperature.

2. A method as claimed in claim 1, wherein the pseudomonic acid or salt thereof is present in the composition in an amount that, in use, exceeds the saturation solubility of the pseudomonic acid or salt in the carrier at ambient temperature.

3. A method as claimed in claim 2, wherein the said amount is at least 150% by weight of the said saturation solubility.

4. A method as claimed in claim 1, wherein the salt of pseudomonic acid is crystalline calcium mupirocin.

5. A method as claimed in claim 1, wherein the pseudomonic acid or salt thereof is present in the composition in an amount of from 0.5 to 10% by weight, based on the total weight of the composition.

6. A method as claimed in claim 5, wherein the pseudomonic acid or salt thereof is present in the composition in an amount of from 1 to 3% by weight, based on the total weight of the composition.

7. A method as claimed in claim 1, wherein the composition comprises from 1 to 3% of mupirocin or a salt thereof, from 65 to 96% of white soft paraffin, from 0 to 15% of liquid paraffin, and from 3 to 7% of lanolin or a derivative or synthetic equivalent thereof.

8. A method as claimed in claim 1, wherein the composition comprises from 1 to 3% of mupirocin or a salt thereof, from 25 to 60% of liquid paraffin, from 20 to 50% of water, and from 3 to 30% of emulsifier.

9. A method as claimed in claim 1, for the treatment of fungal infections caused by filamentous fungi.

10. A method as claimed in claim 1, for the treatment of fungal infections caused by species of Aspergillus, Trichophyton, Trichosporon, Hendersonula, Microsporum, Epidermophyton, and Pityrosporum.

* * * * *